United States Patent [19]
Fischer

[11] Patent Number: 5,364,267
[45] Date of Patent: Nov. 15, 1994

[54] SYRINGE SYSTEM FOR MATCHING TOOTH COMPOSITE COLORS

[75] Inventor: Dan E. Fischer, Sandy, Utah

[73] Assignee: Ultradent Products, Inc., South Jordan, Utah

[21] Appl. No.: 19,266

[22] Filed: Feb. 16, 1993

[51] Int. Cl.5 .............................................. A61C 19/10
[52] U.S. Cl. ...................................... 433/26; 433/90; 206/369
[58] Field of Search ............................ 433/26, 89, 90; 206/571, 63.5, 364, 368, 369

[56] References Cited

U.S. PATENT DOCUMENTS

| | | | |
|---|---|---|---|
| 4,492,576 | 1/1985 | Dragan | 433/90 |
| 4,657,138 | 4/1987 | Watson | 206/571 |
| 4,850,484 | 7/1989 | Denman | 206/571 |
| 5,083,921 | 1/1992 | Dragan | 433/90 |
| 5,199,567 | 4/1993 | Discko, Jr. | 206/368 |

Primary Examiner—Cary E. O'Connor
Attorney, Agent, or Firm—Workman Nydegger Jensen

[57] ABSTRACT

A syringe system for matching tooth composite colors to natural tooth colors. The system includes a plurality of delivery syringes each having therein a different colored tooth composite. A visible portion of each delivery syringe is colored with the same color as the tooth composite within that delivery syringe. Therefore, matching tooth composite color to natural tooth color can be performed by simple viewing of the delivery syringes. An organizer displays the delivery syringes in such a way that the colored portion of each delivery syringe is clearly visible. The organizer also displays the delivery syringes in such way that the delivery syringes together provide a visible palette of colors from which to choose a matching tooth composite.

14 Claims, 7 Drawing Sheets

SYRINGE SYSTEM FOR MATCHING TOOTH COMPOSITE COLORS

BACKGROUND

1. Field of the Invention

The present invention relates to a system for matching tooth color to a tooth composite color. More particularly, the present invention relates to a system for displaying delivery syringes, each containing therein a different colored tooth composite, in such a way that a palette of colors is provided by the display from which to match tooth color to the tooth composite colors within the delivery syringes.

2. Prior State of the Art

Cosmetic and/or functional augmentations of a tooth due to chipping or decay is a common dental procedure. Fortunately, it is a problem that dentists can easily solve. Typically, the dentist will apply a resin-based, light-activated tooth composite to the tooth in order to fill a chipped or missing area. When the tooth composite closely matches the natural color of the tooth, the repair job is barely, if at all, noticeable.

It is critical in this process, however, to accurately match the tooth composite color to the natural tooth. There are many shades of natural tooth colors. Without care, it is possible for the dentist to accidentally apply the wrong tooth composite color.

At present, the method of choosing the matching color of tooth composite is unduly complex and time-consuming, and is subject to the risk of error.

Typically, a color display is used that comprises a rack of artificial or simulated teeth wherein each tooth is a different color. Each artificial tooth in the display is labeled with a code number which identifies the tooth composite color represented by the artificial tooth. The same code number is present on a delivery syringe containing that particular composite color. Once the correct color is decided upon, the user must then note the code number on the artificial tooth, and then retrieve the delivery syringe having thereon the same code number.

One problem with this method is that the codes are often small and difficult to see. As a consequence, the codes on either the colored artificial tooth or the corresponding delivery syringe may be misread, thereby resulting in the wrong choice of syringe. Thus, even if the natural tooth color is accurately matched, misreading of the code numbers can frustrate the job.

Therefore, the process of choosing a correct tooth composite can be time-consuming and must be performed with extra care. As a dentist's time is often in short supply, the extra time necessary for carefully reading the codes on the colored objects and matching those codes with the correct codes on the syringes, and then repeating the process when the codes have been misread, can often be frustrating and burdensome.

Additionally, misplacement or loss of any of the simulated tooth color samples or delivery syringes may further hamper and frustrate the job. It is also often difficult to quickly glance at an assortment of color samples and/or delivery syringes and to easily verify from the code numbers whether duplications and/or omissions of certain colors are present.

BRIEF SUMMARY AND OBJECTS OF THE INVENTION

The present invention seeks to resolve the above and other problems which have been experienced in the art. More particularly, the syringe system of this invention constitutes an important advancement in the art of matching natural tooth colors and using tooth composites, as evidenced by the following objects and advantages realized by the invention over the prior art.

One object of the present invention is to provide a syringe system for conveniently and efficiently matching tooth composite colors to natural tooth colors and obtaining the correct tooth composite in one simple step, without the need of simulated or artificial teeth or other objects.

Another object of the present invention is to provide a system for displaying delivery syringes having different tooth composite colors therein, whereby the color of the tooth composite can be chosen by simply looking at the color of the syringe, thereby eliminating any reference to code numbers and the like.

An additional object of the present invention is to provide a delivery syringe which can be used with a plurality of other similar delivery syringes so as to provide a palette of colors from which to match a patient's tooth color, wherein the color of the tooth composite contained within the syringe matches the color of the syringe, or a portion thereof.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a syringe system is provided for conveniently and efficiently matching the color of a tooth composite to the natural color of a tooth to be repaired.

The syringe system comprises a plurality of delivery syringes, each delivery syringe containing therein a different colored tooth composite, and each delivery syringe being colored so as to match the color of the tooth composite contained therein. The plurality of delivery syringes together provides a palette of colors from which to match a patient's natural tooth color.

Each delivery syringe comprises at least a syringe barrel, a plunger, and a removable cap. The syringe barrel contains therein a tooth composite. Because the tooth composite can be light activated, the syringe barrel must be constructed of an opaque material to prevent light from entering the barrel.

The plunger is sized so as to be able to fit within the syringe barrel and slide longitudinally therein. The plunger is inserted into the syringe barrel and is used to push and extrude the tooth composite material from the syringe barrel.

The removable cap is used to enclose the end of the syringe barrel until such time as the tooth composite is to be extruded from the syringe barrel.

According to the present invention, the syringes, either the entire syringe or a portion thereof, is colored so as to match the color of the tooth composite contained therein. Therefore, the color of the tooth composite can easily be visually perceived simply by looking at the color of the syringe.

An organizing means displays the delivery syringes in such a way that the syringes are prominently visible and accessible for use. The organizing means also displays the syringes in such way that a palette of colors is provided from which to match a patient's natural tooth color.

BRIEF DESCRIPTION OF THE DRAWINGS

In order to more completely understand the manner in which the above-recited and other advantages and objects of the invention are obtained, a more particular description of the invention briefly described above will be rendered by reference to specific embodiments thereof which are illustrated in the appended drawings. Understanding that these drawings depict only presently preferred embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

Figure 1:
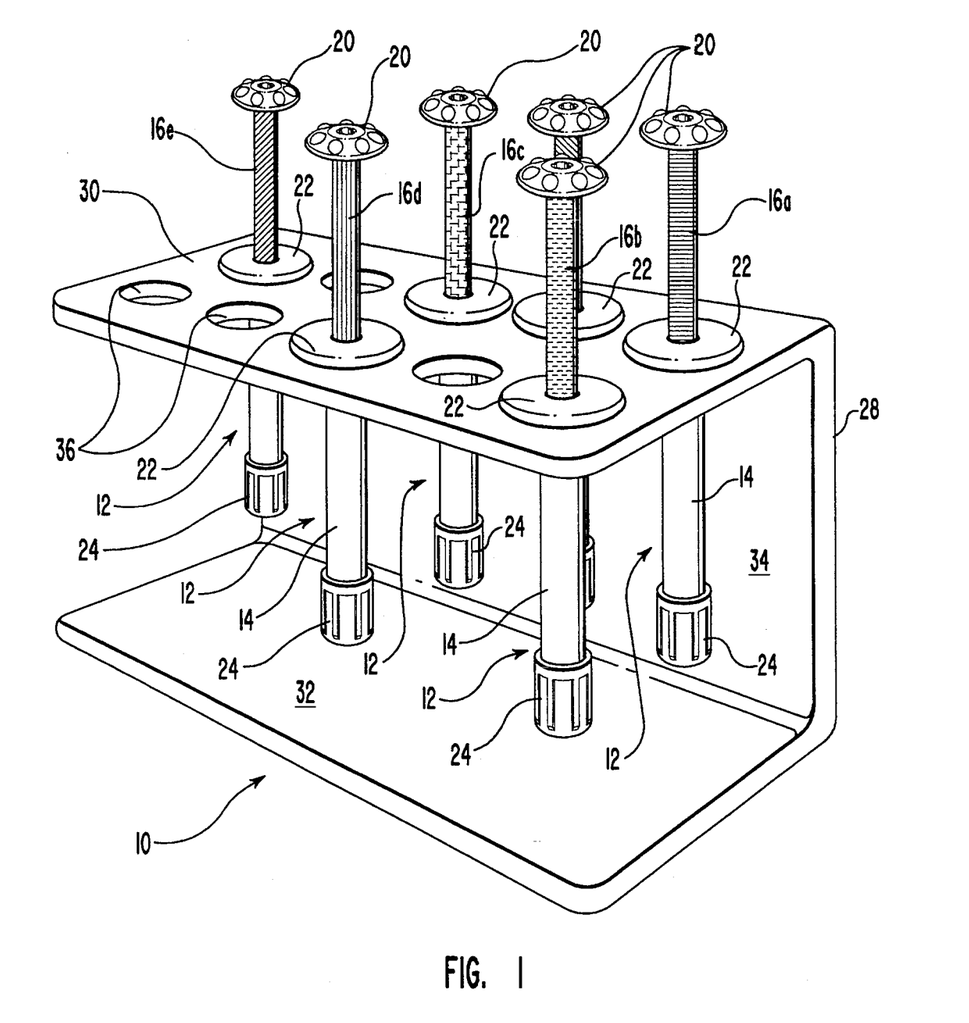
FIG. 1 is a perspective view of one preferred embodiment of the syringe system within the scope of the present invention wherein the plunger of each delivery syringe is colored.

Reference is now made to the drawings wherein like parts are designated with like numerals throughout. Referring first to FIG. 1, one presently preferred embodiment of the syringe system of the present invention is illustrated and generally designated 10.

Syringe System 10 comprises a system for conveniently and efficiently matching tooth composite colors to natural tooth colors. The system comprises a plurality of delivery syringes 12 which each contain therein a different colored tooth composite. Each delivery syringe 12 is colored, in entirety or in part, so as to match the color of the tooth composite contained therein. The plurality of delivery syringes 12 together provides a palette of colors from which to match a patient's natural tooth color.

Each syringe 12 comprises a syringe barrel 14. Syringe barrel 14 is generally cylindrical in shape and is adapted for holding a quantity of a dental composite material. As the material contained therein may be light activated, the syringe barrel 14 is constructed of an opaque material to prevent the passage of light.

Longitudinally slidable within syringe barrel 14 is a plunger 16. An enlarged head 20 is located at the proximal end of the plunger 16. Plunger 16 is slidably contiguous with the inner wall of the syringe barrel 14. In addition, plunger 16 is preferably constructed of a material which is non-reactive with the tooth composite.

At the proximal end of syringe barrel 14 is a circular disk 22. Although conventional syringes function by placing two fingers on the disk 22 and depressing the enlarged head 20 with the thumb, the syringe 12 may also be used by placing the fingers and thumb around the syringe barrel 14 and depressing enlarged head 20 by the palm of the hand.

A removable opaque cap 24 is selectively attachable to the distal end of syringe barrel 14. Removable cap 24 is used for enclosing the end of syringe barrel 14 until such time as the tooth composite is to be extruded from the barrel 14.

As earlier stated, at least one of the parts of each delivery syringe 12 is colored so as to match the color of the tooth composite contained in syringe barrel 14. The color of the tooth composite in each delivery syringe 12 can be thereby visually perceived simply by looking at the coloring of each delivery syringe 12.

Figure 2:
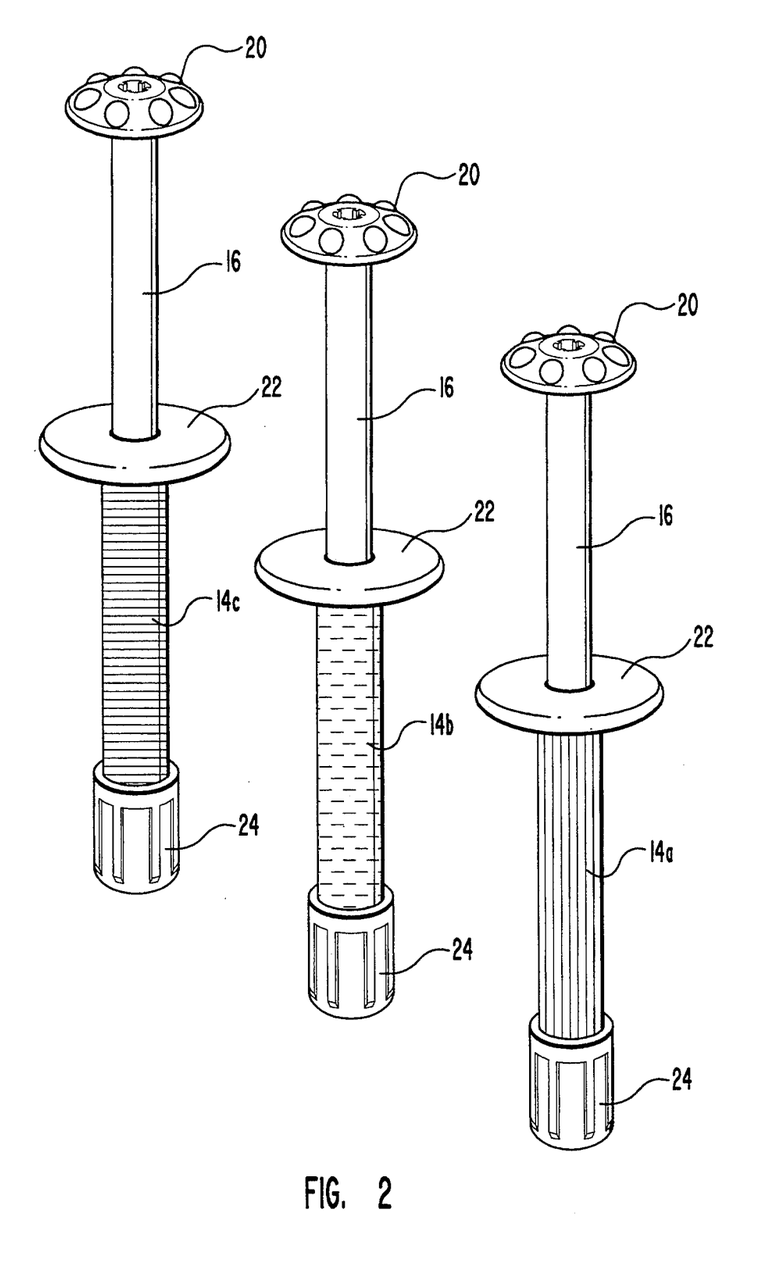
FIG. 2 schematically illustrates another embodiment of the syringe system wherein the entire barrel of each syringe is marked with a color which indicates the color of the tooth composite contained therein.

Various parts of each delivery syringe may be colored. For example, as shown in FIG. 1, the plunger 16a–16e of each delivery syringe 12 may be colored so as to match the color of the tooth composite contained in each particular syringe. As shown in FIG. 2, the entire syringe barrel 14 may be colored. In FIG. 2, three delivery syringes 12 are shown each having a different colored barrel 14a–14c corresponding to the color of the tooth composite within each barrel. When placed together, the syringes provide a palette of colors from which to select a color matching a natural tooth color.

Small portions of each syringe part, as opposed to the entire part, may also be colored. For example, the syringe barrel 14 may be striped with a color which matches the color of the tooth composite contained in that barrel. Further, the finger disks 22 rather than the entire barrel 14, or the enlarged head 20 rather than the entire plunger 16, may be colored.

Figure 3:
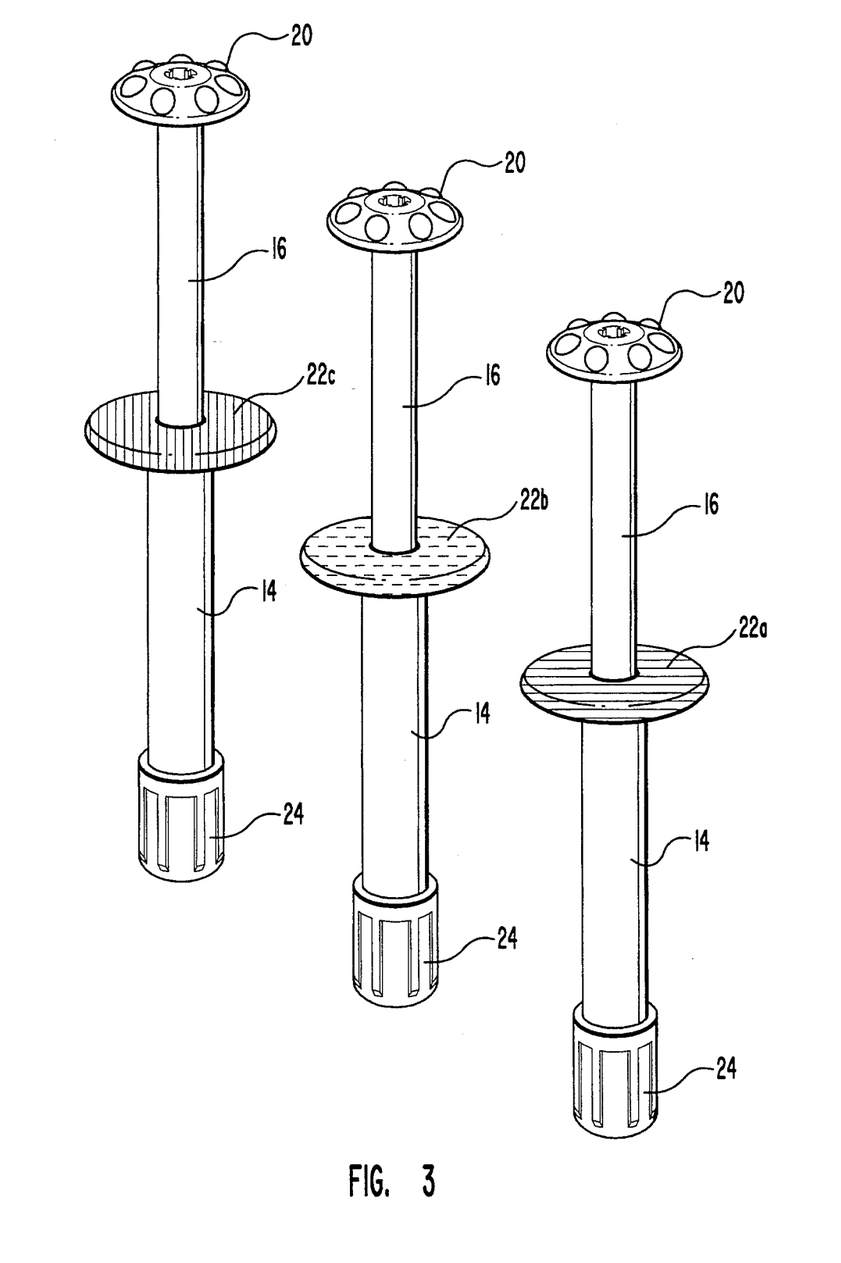
FIG. 3 schematically illustrates yet another embodiment of the syringe system wherein the disks of each syringe is marked with a color which indicates the color of the tooth composite contained within the syringe.
Figure 4:
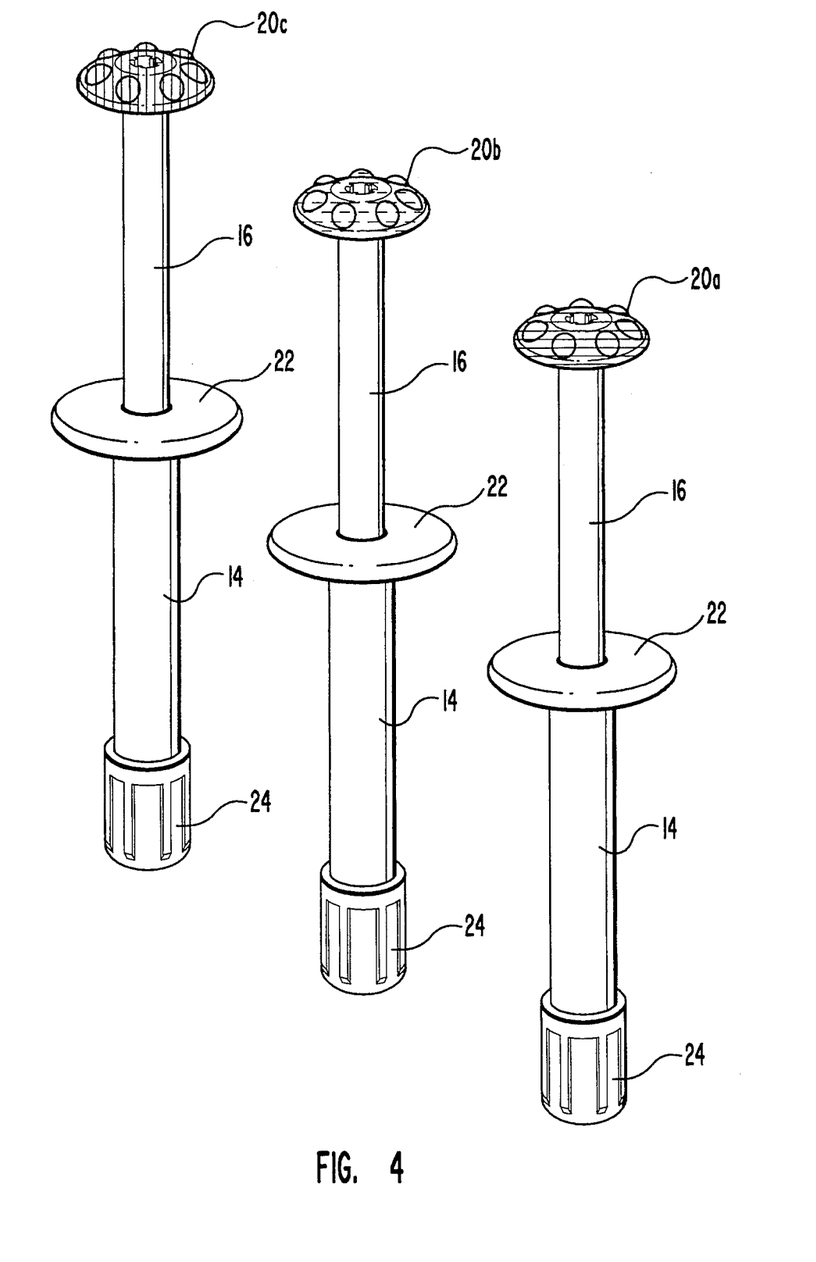
FIG. 4 schematically illustrates yet another embodiment of the syringe system wherein the enlarged head connected to the plunger of each syringe is marked with a color which indicates the color of the tooth composite contained within the syringe.
Figure 5:
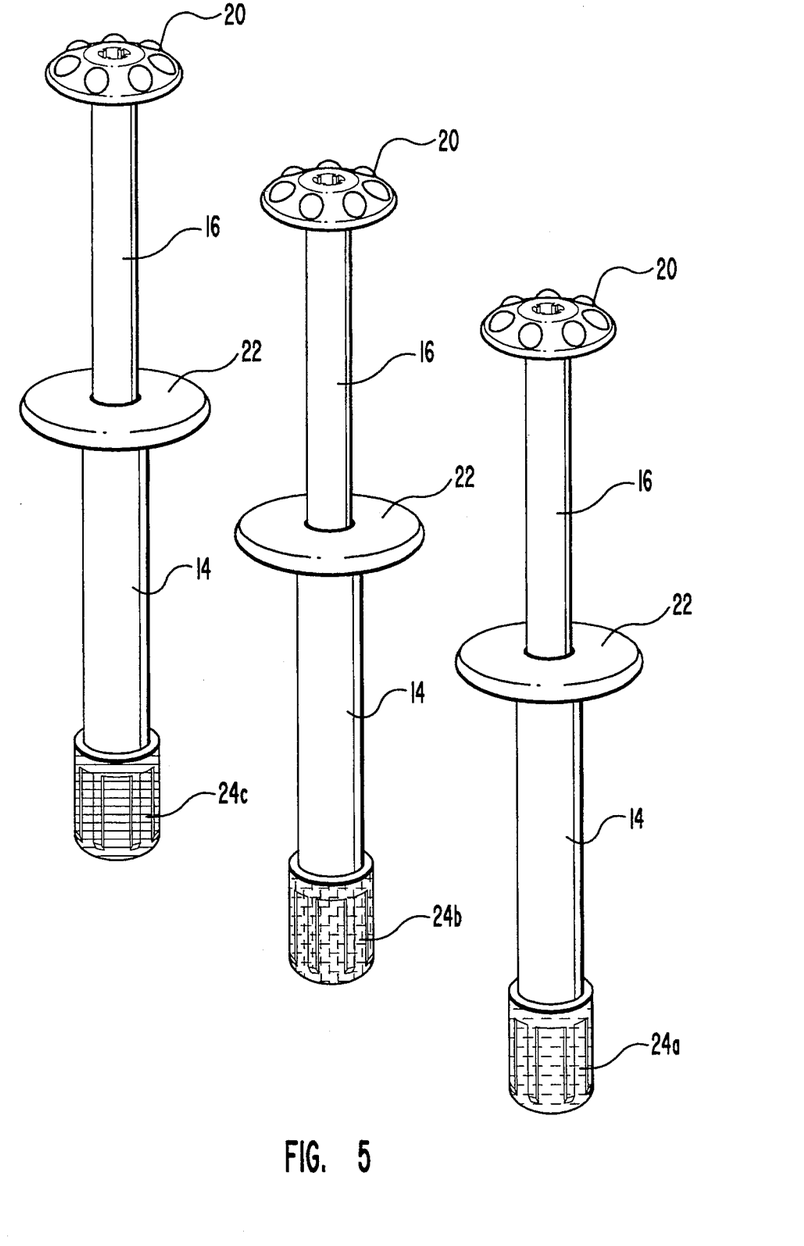
FIG. 5 schematically illustrates yet another embodiment of the syringe system wherein the removable cap of each syringe is marked with a color which indicates the color of the tooth composite contained within the syringe.
Figure 6:
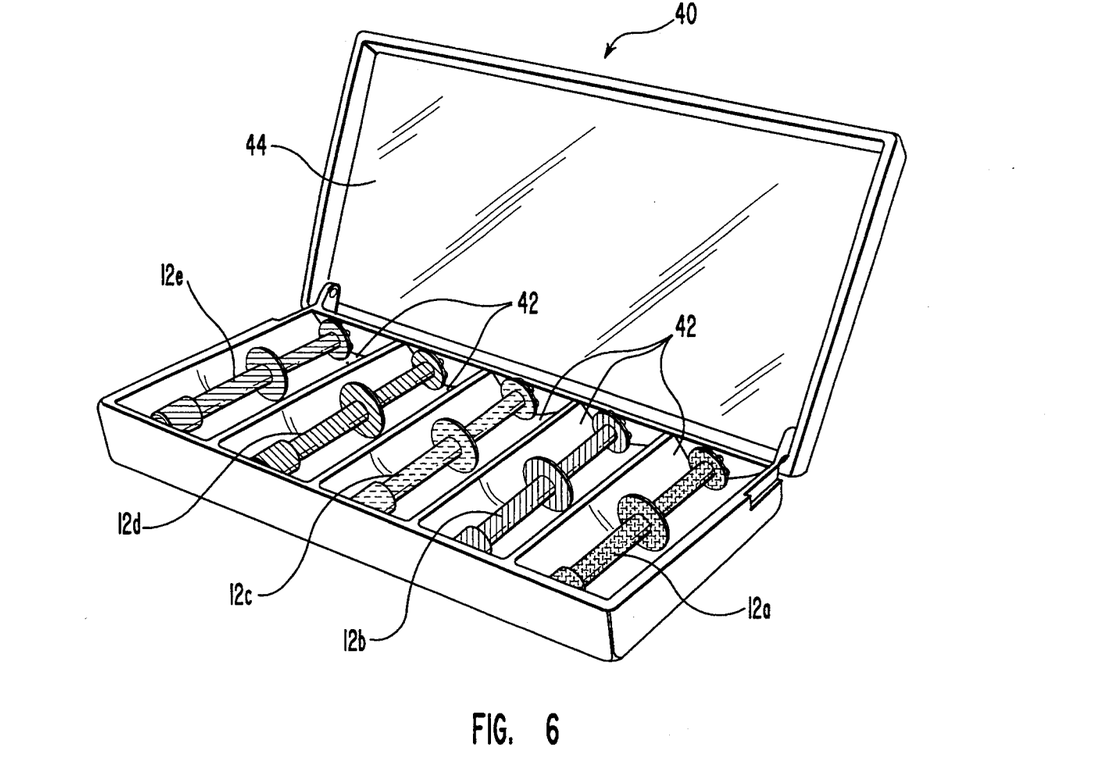
FIG. 6 illustrates an alternate embodiment of the organizing means of the present invention wherein the plurality of syringes are displayed in a transparent box.

In FIG. 3, the disks 22a–22c of three delivery syringes 12 are shown colored in different shades. In FIG. 4, the enlarged heads 20a–20c of each of three delivery syringes 12 is shown to be colored. In FIG. 5, the removable caps 24a–24c of each of three delivery syringes 12 is shown to be colored. In FIG. 6, each syringe 12a–12d is colored in its entirety. In each figure, a range of colors is provided by the different colored syringes.

It can be appreciated that the coloring of a wide variety of parts, and combinations of parts, is possible and within the scope of the present invention. In the preferred embodiment, however, the same part of each delivery syringe is colored. Thus, the delivery syringes can be laid or held side-by-side to display the possible range of colors.

The system of the present invention further comprises organizing means for displaying the plurality of delivery syringes in such a way that the colored portion on each delivery syringe 12 is prominently visible. With this organizing means, matching tooth composite color with natural tooth color is convenient and easy.

Referring back to FIG. 1, one preferred embodiment of the organizing means is illustrated. As illustrated in FIG. 1, the organizing means comprises an organizer 28 having an upper shelf 30 and a bottom support 32. A back wall 34 connects upper shelf 30 and a bottom support 32. Upper shelf 30 is comprised of a plurality of openings 36. Each opening 36 is sized so as to easily allow passage of the syringe barrel 14 of each delivery syringe 12, but prohibit passage of the disk 22. When each delivery syringe 12 is inserted downward into one of the plurality of openings 36, the disk 22 of each delivery syringe 12 is barred from passage through the opening 36 so that each delivery syringe 12 is suspended between the upper shelf 30 and the bottom support 32. While suspended, the colored portion of each delivery syringe 12 can be easily viewed and is held side-by-side in relation to the other syringes 22.

An alternate embodiment of the organizing means of the present invention is illustrated in FIG. 6. A box 40 is shown divided into a plurality of compartments 42. Each compartment 42 is sized such that a delivery syringe 12 fits comfortably therein. A transparent cover 44 may be positioned over box 40 so that the palette of colors provided by the plurality of delivery syringes may be easily viewed, while preventing contamination of the syringes.

It can be appreciated that any organizing means which displays the plurality of delivery syringes 12 such that the colored portions of the delivery syringes are conspicuously visible is within the scope of the present invention.

Further, it is preferred that the organizing means display at least some of the delivery syringes in horizontal alignment so that the colored part of each delivery syringe is held immediately adjacent to the colored part of each adjacent delivery syringe. This provides the optimum view of the palette of colors provided by the display of delivery syringes. The alignment would emphasize the range of colors available from which to match the patient's teeth.

Figure 7:
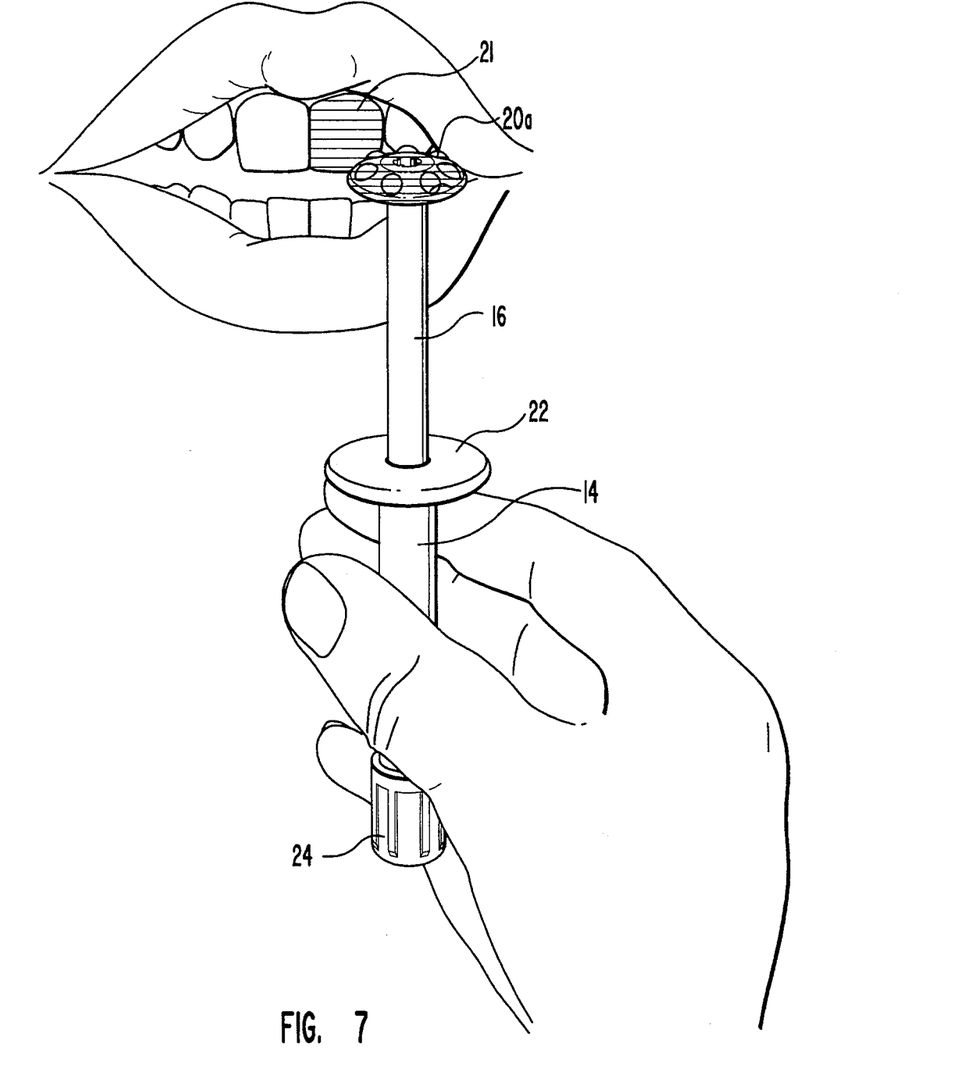
FIG. 7 illustrates a user of the present invention matching the color of a part of a syringe to the natural color of a patient's tooth.

With the system of the present invention, the procedure of matching tooth composite color to a natural tooth color and then obtaining the correct tooth composite color can be accomplished in one step. As illustrated in FIG. 7, each delivery syringe 12 that is selected can be held up to a tooth 21 so as to compare the colored portion 20a of the syringe 12 with the tooth 21. If the color is not matched, another syringe 12 may be compared. If the color is matched, then the syringe 12 and its tooth composite can then be used to perform the required cosmetic or functional augmentation on the matched tooth.

The additional step in the prior art of having to obtain the correct syringe, after the color has first been determined through use of separate comparison objects, is eliminated. With the present invention, choosing the color and obtaining the correct syringe is performed in one step. Valuable time and energy is saved, and the possibility of mistakenly choosing the wrong syringe is virtually eliminated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A syringe system for conveniently and efficiently matching tooth composite colors to natural tooth colors comprising:
    a) a plurality of delivery syringes, each delivery syringe containing therein a different colored tooth composite, and each said delivery syringe comprising at least the following parts:
        a barrel in which the tooth composite is contained and which is constructed of an opaque material to prevent light activation of the tooth composite, said barrel comprising a disk outwardly protruding from the barrel;
        a plunger longitudinally slidable within the barrel for extruding the tooth composite from the barrel; and
        a removable cap for enclosing the end of the barrel until such time as the tooth composite is to be extruded from the barrel;
    b) organizing means for displaying the plurality of delivery syringes such that each delivery syringe is prominently visible and wherein the organizing means is configured such that at least some of the plurality of delivery syringes are displayed in horizontal alignment such that the colored part of each delivery syringe is held immediately adjacent to the colored part of each adjacent delivery syringe and wherein the organizing means comprises a lower support and an upper display shelf said upper shelf being comprised of a plurality of openings, each opening being sized so as to easily allow passage of the barrel of each delivery syringe, but prohibit passage of the disk, such that when each delivery syringe is inserted downward into one of the plurality of openings, the disk of each delivery syringe is barred from passage through the opening so that each delivery syringe is suspended between said upper shelf and said lower support and
    c) wherein at least one of said parts of each delivery syringe is colored so as to match the color of the tooth composite contained in the barrel, whereby the color of the tooth composite in each syringe can be visually perceived simply by looking at the delivery syringes held by the organizing means so that the plurality of delivery syringes together provides a palette of colors from which to match a patient's tooth color.

2. A system as defined in claim 1, wherein the colored part of the delivery syringe comprises at least a portion of the barrel.

3. A system as defined in claim 1, wherein the colored part of the delivery syringe comprises at least a portion of the plunger.

4. A system as defined in claim 1, wherein the colored part of the syringe comprises the removable cap.

5. A system as defined in claim 1, wherein the colored part of the delivery syringe comprises the disk.

6. A system as defined in claim 1, wherein said parts of the delivery syringe further comprises an enlarged head connected to the plunger for use in pushing the plunger into the barrel.

7. A system as defined in claim 6, wherein the colored part of the delivery syringe comprises the enlarged head.

8. A syringe system for conveniently and efficiently matching tooth composite colors to natural tooth colors comprising:
  a) a plurality of delivery syringes, each delivery syringe containing therein a different colored tooth composite, and each said delivery syringe comprising at least the following parts:
    a barrel in which the tooth composite is contained and which is constructed of an opaque material to prevent light activation of the tooth composite, said barrel comprising a disk outwardly protruding from the barrel;
    a plunger longitudinally slidable within the barrel for extruding the tooth composite from the barrel; and
    a removable cap for enclosing the end of the barrel until such time as the tooth composite is to be extruded from the barrel;
  b) organizing means for displaying the plurality of delivery syringes such that each delivery syringe is prominently visible, and wherein the organizing means comprises a lower support and an upper display shelf, said upper shelf being comprised of a plurality of openings, each opening being sized so as to easily allow passage of the barrel of each delivery syringe, but prohibit passage of the disk, such that when each delivery syringe is inserted downward into one of the plurality of openings, the disk of each delivery syringe is barred from passage through the opening so that each delivery syringe is suspended between said upper shelf and said lower support.
  c) wherein at least one of said parts of each delivery syringe is colored so as to match the color of the tooth composite contained in the barrel, whereby the color of the tooth composite in each syringe can be visually perceived simply by looking at the delivery syringes held by the organizing means so that the plurality of delivery syringes together provides a palette of colors from which to match a patient's tooth color; and
  d) wherein the same part of each delivery syringe is colored.

9. A system as defined in claim 8, wherein the colored part of the delivery syringe comprises at least a portion of the barrel.

10. A system as defined in claim 9, wherein the colored part of the delivery syringe comprises the disk.

11. A system as defined in claim 8, wherein the colored part of the delivery system comprises at least a portion of the plunger.

12. A system as defined in claim 11, wherein said parts of the delivery syringe further comprises an enlarged head connected to the stem for use in pushing the plunger into the barrel.

13. A system as defined in claim 12 wherein the colored part of the delivery syringe comprises the enlarged head.

14. A system as defined in claim 8, wherein the colored part of the syringe comprises the removable cap.

* * * * *

UNITED STATES PATENT AND TRADEMARK OFFICE
CERTIFICATE OF CORRECTION

PATENT NO. : 5,364,267
DATED : November 15, 1994
INVENTOR(S) : DAN E. FISCHER

It is certified that error appears in the above-indentified patent and that said Letters Patent is hereby corrected as shown below:

```
Column 6, line 42, after "support" insert --;--
Column 6, line 63, "comprises" should be --comprise--
Column 8, line 2, "." should be --;--
Column 8, line 23, "comprises" should be --comprise--
```

Signed and Sealed this

Twenty-eighth Day of November 1995

Attest:

BRUCE LEHMAN

*Attesting Officer*     *Commissioner of Patents and Trademarks*